United States Patent
Reeder

(10) Patent No.: US 6,827,741 B2
(45) Date of Patent: Dec. 7, 2004

(54) METHOD FOR PREPARING RADIAL AND CARPAL BONES FOR A WRIST PROSTHESIS

(75) Inventor: Nathan Reeder, Georgetown, TX (US)

(73) Assignee: Zimmer Technology, Inc., Chicago, IL (US)

( * ) Notice: Subject to any disclaimer, the term of this patent is extended or adjusted under 35 U.S.C. 154(b) by 20 days.

(21) Appl. No.: 10/339,213

(22) Filed: Jan. 9, 2003

(65) Prior Publication Data

US 2004/0138756 A1 Jul. 15, 2004

(51) Int. Cl.[7] .............................. A61F 2/32; A61F 2/30; A61B 17/34
(52) U.S. Cl. ....................... 623/21.11; 606/80; 606/180
(58) Field of Search .......................... 623/21.11, 21.12, 623/21.13–21.17; 606/79, 84, 87, 180, 80

(56) References Cited

U.S. PATENT DOCUMENTS

| | | | | | |
|---|---|---|---|---|---|
| 4,778,475 A | * | 10/1988 | Ranawat et al. | .......... | 623/23.35 |
| 5,336,226 A | * | 8/1994 | McDaniel et al. | ............ | 606/79 |
| 5,674,223 A | * | 10/1997 | Cipolletti | ...................... | 606/85 |
| 5,702,470 A | * | 12/1997 | Menon | ..................... | 623/21.12 |
| 6,059,832 A | * | 5/2000 | Menon | ..................... | 623/21.15 |
| 6,179,877 B1 | * | 1/2001 | Burke | ..................... | 623/22.12 |
| 6,224,605 B1 | * | 5/2001 | Anderson et al. | ............. | 606/85 |
| 6,620,197 B2 | * | 9/2003 | Maroney et al. | ......... | 623/19.14 |

\* cited by examiner

Primary Examiner—Pedro Philogene
Assistant Examiner—David A Bonderer
(74) Attorney, Agent, or Firm—Jonathan D. Feuchtwang; Zimmer Technology, Inc.

(57) ABSTRACT

A method for preparing and cutting the radial and carpal bones to receive a prosthetic wrist during a total wrist arthroplasty. Cuts on both the radius and carpal bones are made from a single broach. The broach is embedded in the intramedullary canal of the radius and a cutting tool is attached to an end of the broach to resect the radius. With the cutting tool removed, a cut block is attached to the broach and the carpal bones are resected. The cut block has a thickness that equal the thickness of the bearing component of the wrist prosthesis.

18 Claims, 4 Drawing Sheets

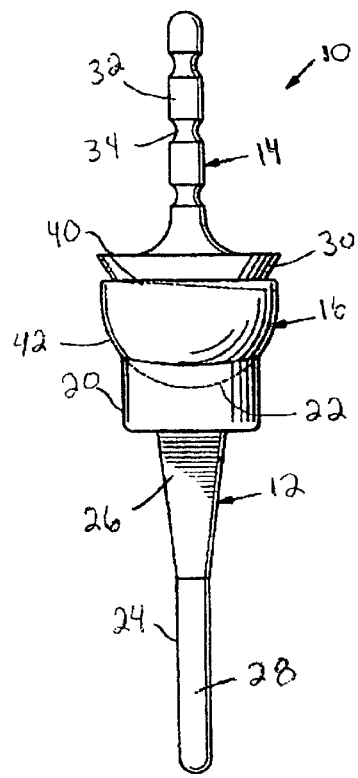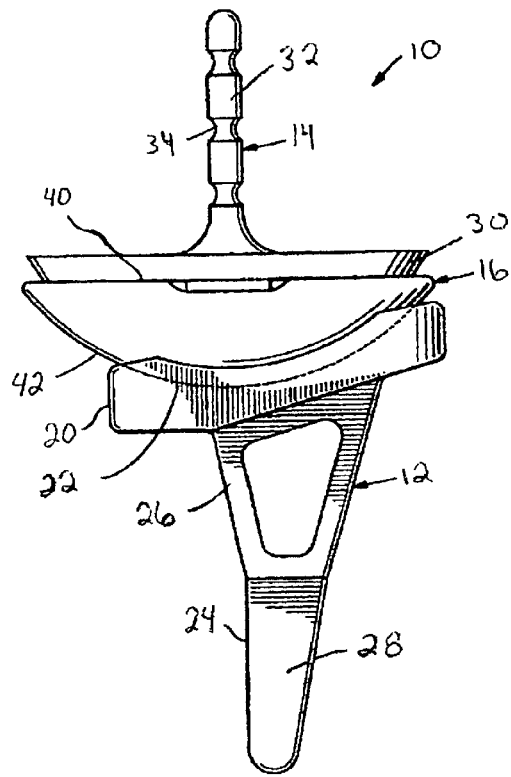
FIG. 1A  FIG. 1B
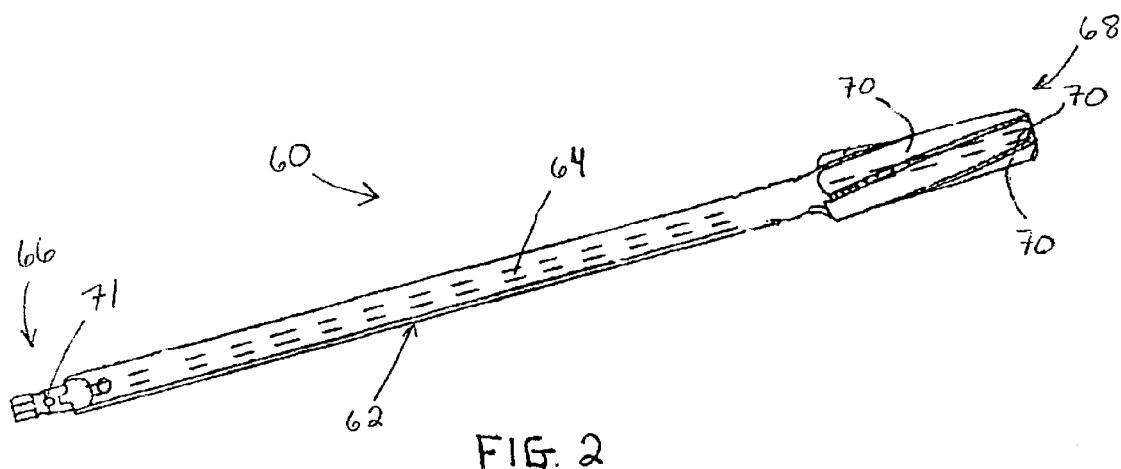
FIG. 2

METHOD FOR PREPARING RADIAL AND CARPAL BONES FOR A WRIST PROSTHESIS

FIELD OF THE INVENTION

The disclosure herein relates generally to implantable orthopedic prosthesis and, more particularly, to new methods for preparing and cutting the radial and carpal bones to receive a wrist prosthesis.

BACKGROUND OF THE INVENTION

Contemporary methods to implant prosthetic wrists have a number of disadvantages. During a total wrist arthroplasty, for example, the intramedullary canal of the radius is reamed and broached, and the end of the radius is cut. The carpal bones are then cut "free-hand." In other words, instruments are often not used to align the cut angles or provide a guide for a planar cut. Further, these cuts are made without using instruments to reference back to cuts made on the radial bone. The cuts on the carpal bone, then, depend heavily on the skill, accuracy, and judgment of the particular surgeon.

One important criteria in wrist arthroplasty is "measured resection." Here, the amount of bone resected should be commensurate with the size of the implant; excessive amounts of bone should not be removed. If too much bone and tissue are removed, the bone can become weak and susceptible to postoperative fracture. If such a fracture occurs, sufficient bone may not remain to permit a satisfactory fusion procedure. Further, the bone may be too weak or too small for subsequent revision or corrective surgical procedures.

As another important criteria in wrist arthroplasty, the cuts on the end of the radial and carpal bones should be made with consistency and precision. If great skill is not used to perform these cuts, the prosthetic wrist implant may not fit well in the bone. As a result, the patient may lose some functionality or experience an unwanted decrease in the range of motion.

The radial and carpal bone cuts are particularly important because prosthetic wrists are manufactured in a limited number of sizes, often +1, +2, and +3 mm. If the cuts are not made in the proper location or with proper alignment, then none of the three sizes of implants may correctly fit.

It therefore would be advantageous to provide new methods for preparing and cutting the radial and carpal bones to receive a wrist prosthesis. Such methods could maximize accuracy and precision of cuts on the carpal and radial bones and simultaneously minimize the amount of bone being resected.

SUMMARY OF THE INVENTION

The present invention is directed toward a method for preparing and cutting the radial and carpal bones to receive a prosthetic wrist during, for example, a total wrist arthroplasty.

One important advantage of the present invention is the amount of bone resected from the radial and carpal bones corresponds to the exact size of the implant to be implanted. Unnecessary bone is not removed. As such, the implant is less susceptible to postoperative fracture due to unwanted bone resection. Further, the prosthetic implant more closely matches the natural wrist and enables a fuller natural range of motion to the patient.

During the first steps of the present invention, the intramedullary canal of the radial bone is reamed. First, a k-wire is placed into the canal, and the position of this wire is visually verified on a fluoroscope. The k-wire, thus, previews the path of the reamer before the canal is reamed. During reaming, the k-wire provides a visual path for the reamer, so the reamer can more successfully be aimed down the canal. The step of using a k-wire helps to ensure that the intramedullary canal of the radial bone is reamed with consistency and precision.

After the canal is reamed, it is broached with a broach having two segments that are removeably connectable to each other. The broach is impacted into the canal, and the handle portion of the broach is removed. A broach segment of the broach, however, is left in the canal. This broach segment is used as both a guide and a reference to cut the end of the radial bone. The broach segment further replicates the actual size of the end of the radial implant to be implanted in the radial bone. Since radial cuts are made with reference to the position of the broach in the intramedullary canal, unnecessary bone is not removed. Further, reference from the broach ensures that the size and shape of the end portion of the radial implant will match the size and shape of the bore in the canal.

In order to perform the cuts on the radial bone, a cutting tool or planer is attached to the broach segment embedded in the canal. The cutting tool is then guided down with the broach segment to cut the end of the radial bone. The cutting tool cuts a plateau or flat surface that matches and aligns with the top, flat surface of the implant.

Next, the carpal bones are cut. In particular, a cut block is connected to the end of the broach segment while it is still embedded in the intramedullary canal of the radius. The cut block has a cutting slot that is aligned to cut the carpal bones in the exact location where the carpal baseplate will be located.

Cutting the carpal bones from the broach segment while it is embedded in the intramedullary canal of the radius has many advantages. For instance, the cut on the end of the carpal bone can be made with consistency and precision. A "free-hand" cut is not used. Further, the cuts on the carpal bone are made while being referenced to the previous cut on the radial bone. Additionally, the cut block has a thickness that exactly matches the size of implant to be implanted. As such, excess bone is not removed from the carpal bones.

BRIEF DESCRIPTION OF THE DRAWINGS

FIG. 1A is a side elevational view of a prosthetic wrist implant.

FIG. 1B is a front elevational view of the prosthetic wrist implant of FIG. 1A.

FIG. 2 is a perspective view of a reamer.

DETAILED DESCRIPTION

Figure 3:
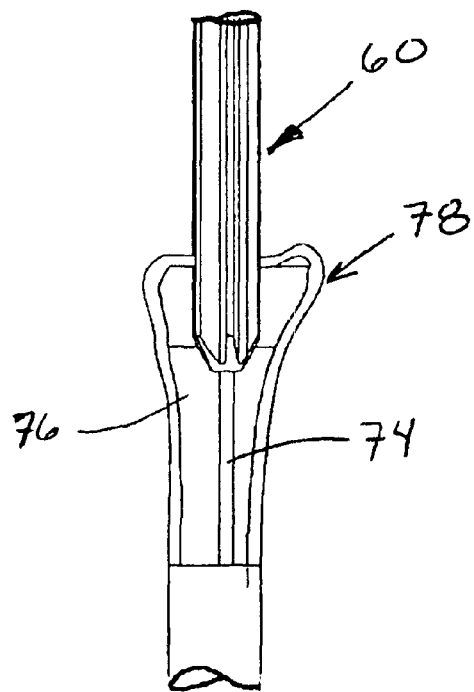
FIG. 3 is a partial cross-sectional view of a reamer reaming an intramedullary canal of a radial wrist bone.

The instruments and methods of the present invention can utilize various prosthetic wrist implants known to those skilled in the art. Generally, the wrist prosthesis consists of three main components: A radial component, a carpal component, and a bearing member. The radial component is formed from metal and has a concave articulation surface and a stem that is implanted into the radius bone. The carpal component includes a metallic base that is implanted into or affixed to the carpal bones, while the bearing member is formed as a polyethylene dome-shaped insert that attaches to the base and articulates with the articulation surface of the radial component.

FIGS. 1A and 1B show an example of one such wrist implant 10, as taught in U.S. Pat. No. 5,702,470, entitled "Prosthetic Wrist Implant and Related Method of Implantation." Wrist implant 10 includes three components: A radial implant 12, a carpal implant 14, and a bearing component 16.

The radial implant 12 includes a bearing guide or head portion 20 with a concave bearing surface 22 and a post or stem 24 tapering downwardly from the head portion. The stem has a proximal portion with a flared body 26 and a distal portion with an elongated tapering configuration 28 that is adapted to be inserted into the intramedullary canal of the radius bone.

The carpal implant 14 has a flat base member 30 and a post member 32. A series of grooves 34 are formed along the exterior of the post member 32 and are adapted to bond with cement and secure the carpal implant firmly in the carpus bone. Peripheral screws (not shown) can extend from the base member and aid in fixing the carpal implant to bone.

One skilled in the art will appreciate that alternate designs exist for carpal and radial implants. The carpal implant, for example, can have several bone screws that extend downwardly from the base member instead of post member 32. Further, portions of the implants could be coated or textured, such as porous coated, to facilitate attachment with bone.

On one side, the bearing component 16 has a flat bottom surface 40 adapted to connect to the base member 30 of the carpal implant 14. Various connections known to those skilled in the art, such as locking tabs and recesses or snap-fits or tapered press-fits, may be used to connect the bearing component and carpal implant. On an opposite side, the bearing component 16 has smooth convex articulating surface 42 adapted to articulate with the concave bearing surface 22 of the radial implant 12. The shape of the bearing component imitates articulation of the lunate and scaphoid bones and provides a functional range of motion of the wrist.

The radial and carpal implants can be made of titanium, titanium alloy, or cobalt chrome alloy; and the bearing member can be made of ultra high molecular weight polyethylene, UHMWPE, such as a polymeric compound Durasul® sold by Centerpulse Orthopedics Inc. of Austin, Tex. One skilled in the art will appreciate that these three components can be made of other metals, polymers, and composites suitable for implantable orthopedic devices.

Further, one skilled in the art will appreciate that various prosthetic wrist implants and instruments (such as reamers, broaches, cut blocks, saw guides, drills, saws, and the like) may be used with the method and steps of the present invention. FIGS. 1A and 1B, for instance, illustrate one type of prosthetic wrist implant that can be utilized with the invention; other wrist implants are known to those skilled in the art.

The instruments, method, and steps of the present invention are now described in more detail. The method describes the steps to perform a surgical procedure for a total wrist arthroplasty. Some of these steps are known to those skilled in the art and will not be discussed in great detail, but one skilled in the art will appreciate that these known steps may be altered or omitted while other known steps may be added. Regardless of the specific steps or techniques used to implant a wrist prosthesis, the novel method and steps of the present invention can be employed in the surgical procedure. As such, the following steps illustrate just one example of how to utilize the novel method and steps of the present invention. Other methods and steps may be employed without departing from the scope of the invention.

As a first step, x-ray templates are used to determine a correct size of wrist prosthesis to be implanted. This procedure can be done under general anesthesia with a tourniquet being used to obtain a bloodless field. Further, this procedure can be done pre-operative to give an indication of the sizes needed, or not done at all. The actual sizes needed can be verified intraoperatively.

A straight incision is made on the skin along the third metacarpal bone of the wrist. Skin and tissue surrounding the incision are retracted using, for example, silk retraction sutures. The extensor retinaculum can now be opened, and a dorsal synovectomy can be performed. With the wrist in this position, various tendons can be examined for functionality and integrity.

Next, the radial bone is prepared for resection using techniques known to those skilled in the art. The joint capsule is detached, and the brachioradialis and the tendons from the dorsal compartment muscles are elevated. Next, the posterior intraosseous nerve can be resected and accompanying vessels cauterized to reduce fluid flow. Retractors can be used to protect the sutures, and the wrist can be safely flexed.

One of the novel steps of the present invention is to ensure that the intramedullary canal of the radius is properly or accurately reamed. To achieve this result, a k-wire is inserted into the intramedullary canal of the radius. The correct orientation and location of the k-wire can be verified with a fluoroscope. Next, a cannulated reamer is placed over the k-wire, and the intramedullary canal is reamed.

FIG. 2 shows an example of a cannulated reamer 60 according to the present invention. Reamer 60 has an elongated body 62 with a longitudinal bore or channel 64 that extends completely through the body from a proximal end 66 to a distal end 68. The distal end 68 includes a plurality of longitudinal cutting flutes 70 disposed along the exterior of the body 62. These flutes are adapted to ream bone while inserted into the intramedullary canal. The proximal end 66 includes a tool engaging mechanism 71 adapted to engage a motorized drive tool (not shown).

Looking now to FIGS. 2 and 3, the steps are announced in more detail. A k-wire 74 is first inserted into the intramedullary canal 76 of radial bone 78. The position and location of the wire is then verified using a fluoroscope. Once verification is made that the k-wire is in the correct position, the wire is placed in the bore 64 of the reamer 60. The reamer is then moved downwardly into the canal 76. Since the k-wire is properly oriented in the canal and this orientation was verified with a fluoroscope, proper reaming of the canal can be ensured. Additionally, and as further verification of a proper reaming location, the fluoroscope can be used to verify the position of the reamer as it passes down the canal and reams bone.

The reamer creates a longitudinal bore in the canal that is shaped to receive the elongated stem of the radial implant. A proximal portion of the canal must now be prepared to receive the flared body or proximal portion of the radial implant.

Figure 4:
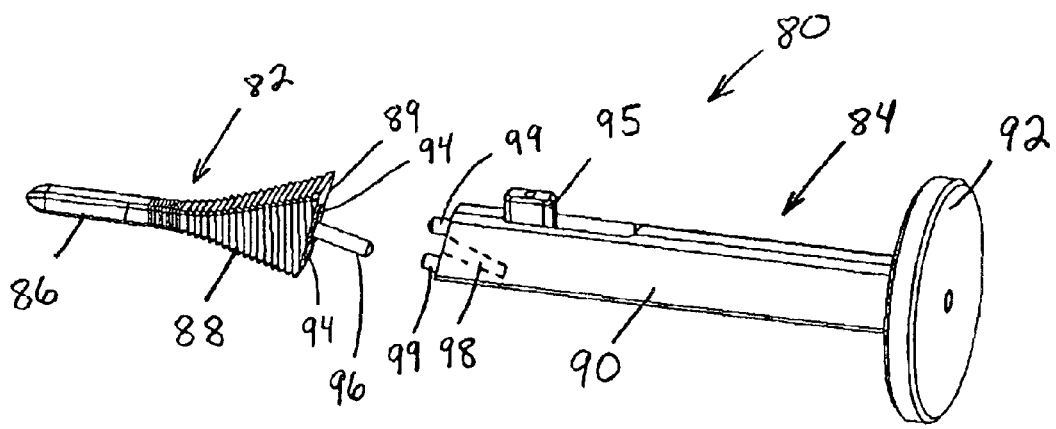
FIG. 4 is an exploded perspective view of a two-piece broach having a broach segment and a handle segment.

FIG. 4 shows a broach 80 that is adapted to prepare the proximal portion of the intramedullary canal to receive the radial implant. Broach 80 includes two separate pieces, a broach segment 82 and a handle segment 84.

Broach segment 82 has a distal portion with an elongated cylindrical or square shaft 86 and a proximal portion with cutting teeth 88 along the exterior of the body. A large flat or planar surface 89 is disposed at the end of the proximal portion. The shaft 86 is adapted to guide the broach down the bore of the intramedullary canal while the teeth 88 are adapted to cut into bone. The proximal portion is shaped to match the flared body 26 or proximal portion of radial implant 12 (shown in FIG. 1).

Handle segment 84 has an elongated body 90 extending from a distal end to a proximal end. The proximal end has a flat disk or impaction surface 92 adapted to impact with a mallet or hammer for driving the broach into bone.

As shown, the broach 80 is formed as two separate and distinct components that are removeably connected together. Broach segment 82 and handle segment 84 can be removeably connectable with a variety of means known to those skilled in the art. FIG. 4 shows one example wherein the proximal end of the broach segment 82 includes two cylindrical bores 94 and an elongated cylindrical projection 96 extending outwardly from the planar surface 89. The distal end of the handle segment has a single elongated cylindrical bore 98 and two cylindrical projections 99 extending outwardly. The two bores 94 and cylindrical projection 96 are adapted to engage and mate with the corresponding two projections 99 and elongated bore 98, respectively, to removeably connect the broach segment 82 to the handle segment 84. A disconnect button 95 is located at the distal end of the handle segment to release the two segments.

Once the reamer is removed from the bone, the shaft 86 of broach 80 is placed in the intramedullary canal. The broach is then pounded or impacted (either manually or with a motorized tool) to a desired depth in the canal. At this point, it is important to note that the depth and orientation of the broach segment should replicate the depth and orientation of placement of the radial implant. In other words, the position of the broach segment mimics the position of the radial implant since the proximal portion of the radial implant has a size and shape to match the broach segment. Once the correct orientation of the broach is achieved in the intramedullary canal, the handle segment 84 is detached or removed from the broach segment 82. The broach segment 82 is thus left pounded or embedded into the bone with the planar surface 89 exposed at the proximal end of the intramedullary canal. The articulating surface of the radial bone is ready to be osteotomized and removed.

Figure 5:
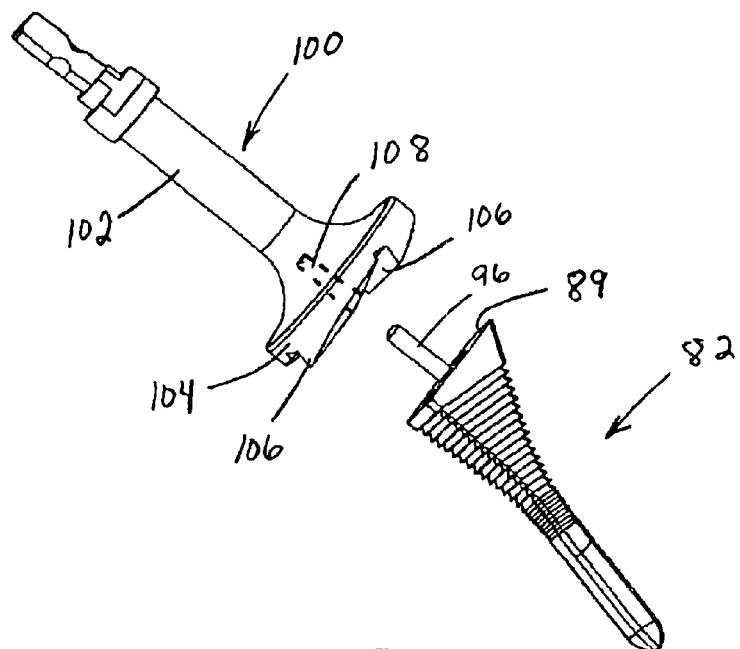
FIG. 5 is an exploded perspective view of the broach segment of FIG. 4 and a cutting tool.

FIG. 5 shows the broach segment 82 and a cutting tool or planer 100 having an elongated drive shaft 102 that terminates in an enlarged head 104. The head 104 has a cylindrical shape with a plurality of cutting flutes 106 disposed on a distal surface. The flutes are adapted to cut or remove bone while the planer is rotated. A cylindrical recess 108 extends in a longitudinal direction into the head 104 and is adapted to receive or engage the projection 96 on the broach segment 82.

During use, the recess 108 of planer 100 is placed over the projection 96 of broach segment 82 so the planer can slideably engage the projection while cutting the radial bone. The planer is guided downwardly until the cutting flutes 106 contact the flat surface 89. As the planer moves downwardly, it cuts bone; and a flat or planar surface is thus created at the proximal end of the intramedullary canal at the surface 89 of the broach segment 82.

These steps of using broach and planer to cut a plateau or planar surface on the radius represent an important advantage of the present invention. The planer is able to cut or plane a plateau or planar surface while simultaneously referencing the position and orientation of the broach segment that is embedded in the intramedullary canal of the radial bone. The position and orientation of the broach segment replicates the position and orientation of the radial implant once the implant is positioned into the canal. As a further advantage, a "free-hand" cut at the end of the radial bone is not necessary since the planer is guided to cut the radial bone with the broach segment.

Figure 6:
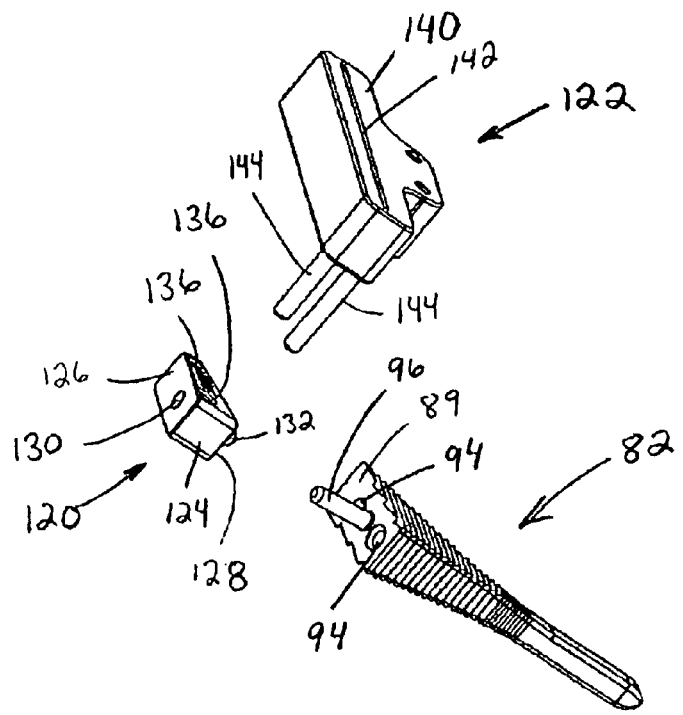
FIG. 6 is an exploded perspective view of the broach segment of FIG. 4 and an adapter and cut block.

FIG. 6 shows broach segment 82 and an adapter 120 and cut block 122 used in accordance with the method of the present invention. The adapter 120 has a body 124 with a proximal surface 126 and a distal surface 128. Distal surface 128 is sized and shaped to match the planar surface 89 of broach segment 82. The body 124 includes a cylindrical recess 130 adapted to receive the projection 96 of broach segment 82. Two parallel spaced alignment rods or extensions 132 (one being shown) project outwardly from the body 124 and are adapted to be inserted into the two bores 94 at the proximal end of the broach segment. Further, two parallel, cylindrical bores or channels 136 extend completely through the body 124.

Cut block 122 has a rectangular body 140 with an elongated, thin cutting slot 142 adapted to receive a saw blade (not shown). Two parallel posts or projections 144 extend outwardly from the body 140. The posts are sized to fit into the two channels 136 on the adapter so the adapter and cut block can be removeably connected together.

After the radial bone is cut, the broach segment 82 is left embedded in the intramedullary canal. Adapter 120 is then connected to the proximal end of the broach segment with the distal surface 128 of the adapter contacting the planar surface 89 of the broach segment. Specifically, the alignment rods 132 are positioned into the two bores 94, and the post 96 slides into the hole or recess 130. Next, the cut block 122 is attached to the adapter 120. Specifically, the posts 144 are slideably positioned in the channels 136.

With the cut block and adapter attached to the proximal end of the broach segment, the carpal bones can be prepared with techniques known to those skilled in the art. Such preparation can include, for example, applying traction to the hand to move the carpal bone from under the radius, flexing the wrist to about 80°, and removing or moving cartilage from articular surfaces.

It will be appreciated by those skilled in the art that the carpal bones may be prepared before or after the adapter and cut block are attached to the broach segment.

After the carpal bones are prepared, a saw blade (not shown) is inserted through the cutting slot 142 of the cut block, and the carpal bones are resected.

Although FIG. 6 shows an adapter and cut block that are connectable to the distal end of the broach segment, it will be appreciated that the cut block can be configured to be attached to the broach segment without the use of the adapter.

Figure 7:
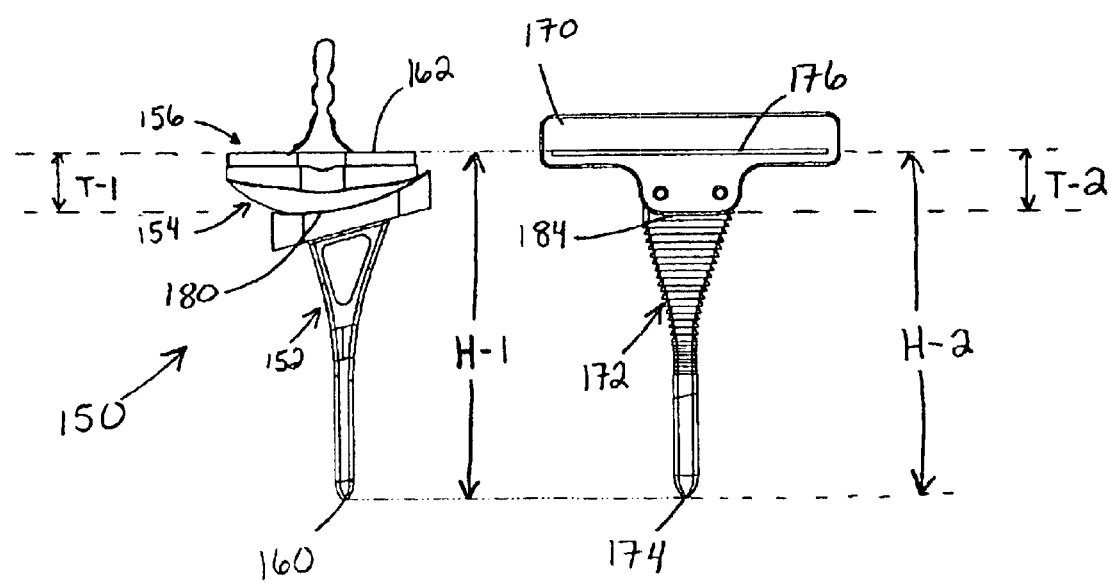
FIG. 7 is a side view of an assembled prosthetic wrist implant next to a side view of an assembled broach segment, adapter, and cut block.

Looking now to FIG. 7, a wrist implant 150 is shown assembled and includes a radial implant 152, a bearing component 154, and a carpal implant 156. Wrist implant 150 when assembled has a total height "H-1" that extends from a distal tip 160 of the radial implant 152 to a planar or top surface 162 of the carpal implant 156.

FIG. 7 also shows a cut block 170 connected to a broach segment 172 as described in connection with FIG. 6. The assembly has a cutting height "H-2" that extends from a distal tip 174 of the broach segment to the cutting slot 176 of the cut block.

One important advantage of the present invention is that the total height H-1 of the assembled wrist implant 150 is exactly equal to the cutting height H-2 of the assembled broach segment 172 and cut block 170. These equal heights ensure "measured resection" is achieved during wrist arthroplasty. In other words, the amount of bone resected from the radial and carpal bones is exactly commensurate with or equal to the size of the wrist implant to be implanted. The location of the cutting slot 176 is thus positioned to cut the carpal bone exactly where the top surface 162 of the carpal implant will reside once implanted.

FIG. 7 also illustrates that the assembled bearing component 154 and carpal implant 156 have a thickness "T-1" that extends from the tip of the articulating surface 180 of the bearing component to the planar surface 162 of the carpal implant. Further, the cut block 170 has a thickness "T-2" that extends from a distal surface 184 (located at the top surface of the broach) to the cutting slot 176. The thickness T-1 is equal to the thickness T-2.

It will be appreciated that the wrist implant of the present invention can be manufactured in numerous sizes. These sizes can have different total heights H-1 or different thicknesses T-1. Preferably, for each height H-1 a corresponding assembled broach segment and cut block have a cutting height H-2 wherein H-1 equals H-2 for each size of wrist implant. Further, for each thickness T-1, a corresponding cut block has a thickness T-2, where in T-1 equals T-2. As an example, the bearing component may be offered in three different sizes, corresponding to thickness designated as +1, +2, and +3 mm. In this situation, the cut block could be manufactured to have three different thickness as +1, +2, and +3 mm to match the sizes of the bearing components.

Turning back now to the method of the present invention, once the carpal cuts are made, the adapter and cut block are removed from the end of the broach segment. The handle segment is then re-attached to the broach segment, and the entire broach is removed from the intramedullary canal.

At this stage, the wrist prosthesis is implanted using techniques or steps known to those skilled in the art. For a cement retained prosthesis, a possible technique, for example, may include some or all of the following steps: In order to install the carpal implant, the osteotomy is irrigated with a pulsed lavage, and then bone cement (such as PMMA) is introduced into the capitate metacarpal complex. The stem of the carpal implant is then placed in the bore and tapped or pushed to the desired depth and location. Bone screws (if applicable) can be inserted through the carpal plate to more securely fix the carpal implant. Any excess cement should be wiped or otherwise removed. Further, cancellous bone graphs, such as those from the radius and resected carpal bones, can be packed into defects around the carpal bones to enhance bone fusion.

In order to install, the radial implant, a cement restrictor or bone plug can be placed into the intramedullary canal to restrict the distal flow of bone cement. The osteotomy is irrigated with a pulsed lavage, and bone cement is introduced into the canal. The radial implant is then placed in the bore and tapped or pushed to the desired depth and location. The prosthesis should be placed in a valgus position, and excess cement should be wiped or otherwise removed.

Next, the bearing component is attached to the carpal baseplate. This connection can be made using various techniques and configurations known to those skilled in the art. Preferably, the bearing component is snap-locked to the baseplate.

Next, verification is made that the carpal implant and bearing component are correctly attached and match the position and orientation of the bearing or articulating surface of the radial implant. The wrist joint should be tested for range of motion as well.

As a final step, the wound can be closed in accordance with techniques and steps known to those skilled in the art. Typically, the ulnar joint capsule is closed, the ECU tendon moved dorsally, and the radial carpal joint is re-attached. The hand is placed in a neutral position and then immobilized with a dressing and cast.

It should be emphasized that although the method of the present invention was described with a specific number and sequence of steps, these steps can be altered without departing from the scope of the invention.

It should be emphasized that although the method of the present invention was described with a specific number and sequence of steps, these steps can be altered without departing from the scope of the invention.

Although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for implanting a prosthetic wrist, comprising the steps of:
    providing a reamer;
    providing a broach having two separable components, a handle segment at a proximal end and a broach segment at a distal end;
    providing a cutting tool;
    providing a cut block;
    reaming an intramedullary canal of a radial bone with the reamer;
    broaching the intramedullary canal with the broach;
    removing the handle segment from the broach segment while the breach segment is embedded in the intramedullary canal;
    leaving the broach segment embedded in the intramedullary canal;
    guiding the cutting tool with the broach segment to cut the radial bone;
    attaching the cut block to the broach segment while the broach segment is still embedded in the intramedullary canal;
    using the cut block to guide cutting of a carpal bone;
    removing the cut block and broach segment from the intramedullary canal; and
    implanting the prosthetic wrist.

2. The method of claim 1 further comprising the step of slideably engaging the cutting tool and the broach segment while cutting the radial bone.

3. The method of claim 1 further comprising the steps of:
    providing an adapter;
    placing the adapter on the broach segment before the step of attaching the cut block;
    attaching the cut block to the adapter; and
    removing the adapter during the step of removing the cut block and broach segment from the intramedullary canal.

4. The method of claim 1 further comprising the step of referencing a position and orientation of the broach segment while embedded in the intramedullary canal to cut the radial bone.

5. The method of claim 4 further comprising the step of using the cutting tool to perform the step of referencing a position and orientation of the broach segment.

6. The method of claim 1 in which the step of using the cut block to guide cutting of a carpal bone further includes the step of inserting a saw blade through a cutting slot located on the cut block.

7. The method of claim 1 further comprising the step of referencing a position and orientation of the broach segment while embedded in the intramedullary canal to cut the carpal bone.

8. A method for cutting a radial and carpal bone to implant a wrist prosthesis, comprising the steps of:
reaming the radial bone;
broaching the radial bone with a broach;
leaving the broach embedded in the radial bone;
attaching a cutting tool to the broach while the broach is embedded in the radial bone;
cutting the radial bone with the cutting tool;
removing the cutting tool from the broach;
attaching a cut block to the broach while the broach is embedded in the radial bone;
engaging a saw with the cut block;
cutting the carpal bone with the saw;
removing the saw from the cut block; and
removing the cut block and broach from the radial bone.

9. The method of claim 8 further comprising the step of removing a segment of the broach after the step of broaching the radial bone.

10. The method of claim 8 further comprising the step of providing the broach with a handle segment and a broach segment, wherein the handle segment is removable from the broach segment.

11. The method of claim 10 further comprising the step of leaving the broach segment embedded in bone and detaching the handle segment.

12. The method of claim 11 further comprising the step of attaching the cut block to the broach segment during the step of attaching a cut block to the broach while the broach is embedded in the radial bone.

13. The method of claim 8 further comprising the step of slideably engaging the cutting tool with the broach to cut a planar surface on the radial bone during the step of cutting the radial bone with a cutting tool.

14. The method of claim 13 further comprising the steps of:
providing the broach with a flat surface at a proximal end; and
cutting the planar surface at the flat surface of the broach.

15. A method for cutting a radial bone to implant a wrist prosthesis, comprising the steps of:
providing a broach with a handle segment and a broach segment, the handle segment being removable from the broach segment;
broaching an intramedullary canal of the radial bone by impacting the handle segment to drive the broach segment into the intramedullary canal;
removing the handle segment from the broach segment while leaving the broach segment embedded in the intramedullary canal;
attaching a cutting tool to the broach segment while the broach segment is embedded in the intramedullary canal;
cutting the radial bone with the cutting tool while the cutting tool is attached to the broach segment;
providing the broach segment with a flat surface at a proximal end;
cutting the radial bone with the cutting tool until the cutting tool contacts the flat surface; and
using the broach segment to guide the cutting tool during the step of cutting the radial bone with the cutting tool.

16. A method for cutting a radial bone to implant a wrist prosthesis, comprising the steps of:
providing a broach with a handle segment and a broach segment, the handle segment being removable from the broach segment;
broaching an intramedullary canal of the radial bone by impacting the handle segment to drive the broach segment into the intramedullary canal; removing the handle segment from the broach segment while leaving the broach segment embedded in the intramedullary canal;
attaching a cutting tool to the broach segment while the broach segment is embedded in the intramedullary canal; and
cutting the radial bone with the cutting tool while the cutting tool is attached to the broach segment;
providing a cut block;
removing the cutting tool from the broach segment after the step of cutting the radial bone with the cutting tool;
attaching the cut block to the broach segment while the broach segment is embedded in the intramedullary canal; and
cutting the carpal bone while the cut block is attached to the broach segment.

17. The method of claim 16 further comprising the steps of:
removing the cut block from the broach segment;
removing the broach segment from the intramedullary canal; and
implanting the wrist prosthesis in the radial and carpal bones.

18. The method of claim 16 further comprising the steps of:
providing the cut block with a thickness that extends from a top surface on the broach segment to a cutting slot on the cut block;
providing the wrist prosthesis with a thickness that extends from a tip of an articulating surface of a carpal implant to a planar surface of the carpal implant; and
providing the thickness of the cut block to be equal to the thickness of the wrist prosthesis.

* * * * *